United States Patent
Deichmann et al.

(10) Patent No.: US 10,052,184 B2
(45) Date of Patent: Aug. 21, 2018

(54) SURGICAL IMPLANT

(71) Applicant: Johnson & Johnson Medical GmbH, Somerville, NJ (US)

(72) Inventors: Thorsten Deichmann, Lubeck (DE); Jorg Priewe, Kiel (DE)

(73) Assignee: Johnson & Johnson Medical GMBH, Norderstedt (DE)

(*) Notice: Subject to any disclaimer, the term of this patent is extended or adjusted under 35 U.S.C. 154(b) by 428 days.

(21) Appl. No.: 14/190,512

(22) Filed: Feb. 26, 2014

(65) Prior Publication Data

US 2014/0257517 A1 Sep. 11, 2014

(30) Foreign Application Priority Data

Mar. 20, 2013 (DE) .................. 10 2013 004 573

(51) Int. Cl.
*A61F 2/00* (2006.01)
*B29C 70/68* (2006.01)

(52) U.S. Cl.
CPC .......... *A61F 2/0063* (2013.01); *A61F 2/0077* (2013.01); *B29C 70/68* (2013.01)

(58) Field of Classification Search
CPC ................. A61F 2/0063; A61F 2/0077
See application file for complete search history.

(56) References Cited

U.S. PATENT DOCUMENTS

| 7,331,199 | B2 | 2/2008 | Ory et al. |
| 8,123,817 | B2* | 2/2012 | Intoccia ............... A61F 2/0045 |
| | | | 606/151 |
| 2002/0077661 | A1 | 6/2002 | Saadat |
| 2006/0252981 | A1* | 11/2006 | Matsuda ................ B32B 7/02 |
| | | | 600/37 |
| 2011/0257666 | A1* | 10/2011 | Ladet .................... A61L 27/48 |
| | | | 606/151 |
| 2012/0197415 | A1* | 8/2012 | Montanari ........... A61F 2/0063 |
| | | | 623/23.74 |
| 2012/0209227 | A1* | 8/2012 | Dunn .................. A61M 1/0088 |
| | | | 604/319 |

FOREIGN PATENT DOCUMENTS

| DE | 102012005978 | 3/2012 |
| WO | WO 03/099160 | * 12/2003 |
| WO | WO 2003/099160 | 12/2003 |
| WO | WO 2006/092236 | 9/2006 |
| WO | WO 2011/026987 | 3/2011 |

* cited by examiner

*Primary Examiner* — Julie S Szpira
(74) *Attorney, Agent, or Firm* — E. Richard Skula

(57) ABSTRACT

A surgical implant (1) comprises a basic structure (2) having a first face (4) and a resorbable film (6) attached to the first face (4) of the basic structure (2). A plurality of solid protrusions (8) emerges from the film (6) in a direction away from the basic structure (2). The protrusions (8) comprise a shape defined by a respective body and a respective head, the body emerging from the film (6) and terminating in the head, and the head projecting laterally with respect to the body.

18 Claims, 7 Drawing Sheets

Figure 1:
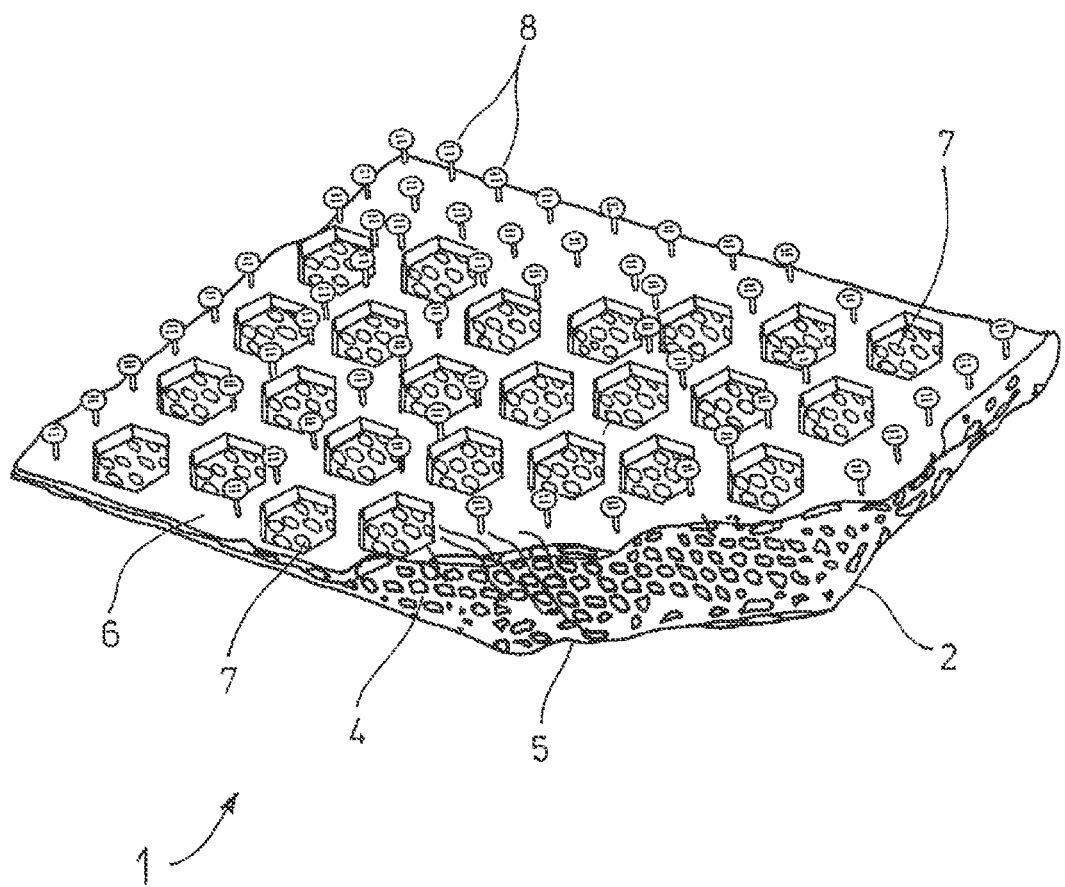

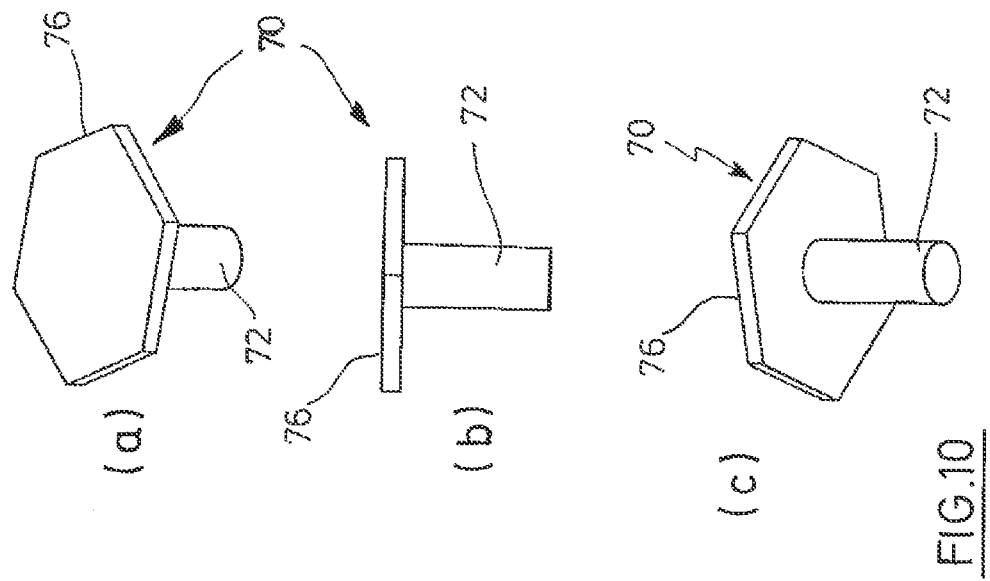
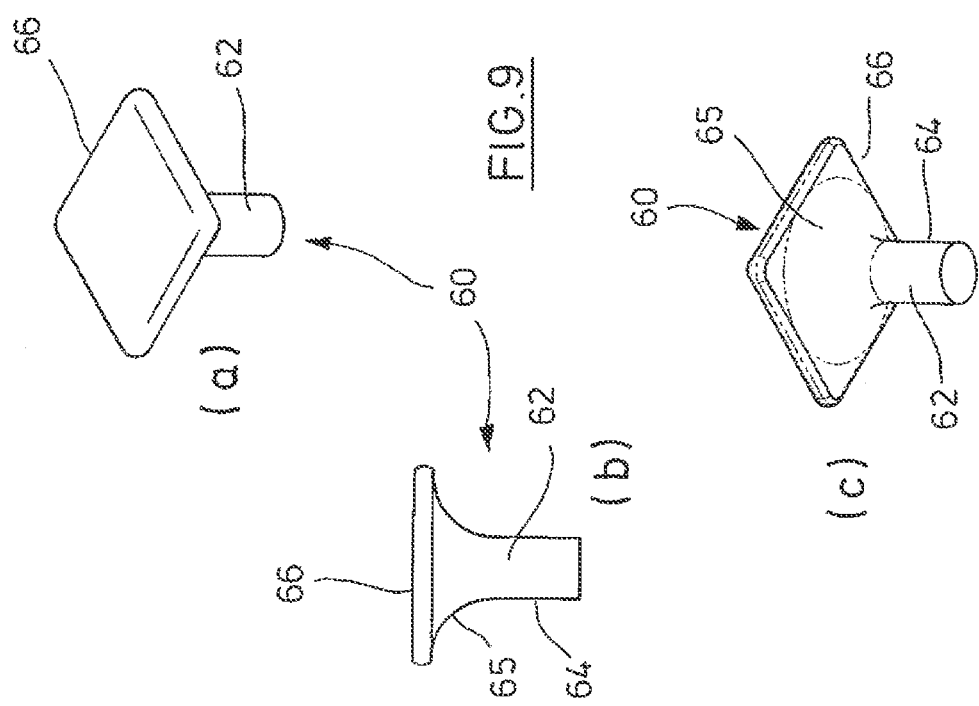

SURGICAL IMPLANT

CROSS REFERENCE TO RELATED APPLICATIONS

This application claims priority from German Patent Application DE 102013004573.8 filed Mar. 11, 2013 the disclosure of which is hereby incorporated by reference in its entirety.

The invention relates to a surgical implant, in particular to a tissue reinforcing implant for repair of inguinal hernias and/or ventral/incisional hernias.

Hernia repair is one of the most common surgical procedures, with approximately 6.4 million procedures performed globally every year. Approximately 3.1 million hernias (48%) are repaired with flat mesh annually.

The mesh serving as a surgical implant reinforces the area of the hernia. To achieve a safe fixation, the mesh can be sutured to the bodily tissue close to the hernia. However, the suturing step delays the surgical procedure and can cause post-surgical pain to the patient, e.g. due to nerve damage.

WO 2003/099160 A discloses a surgical implant comprising a knobbed film which can be connected to a surgical mesh. The knobs are hollow and increase the flexibility of the film. The knobbed film can be produced from a resorbable polymer film using a thermal deforming process. Depending on the design, the knobs may increase or decrease the friction between the implant and the bodily tissue, thus achieving a fixation effect or enhanced mobility, respectively.

WO 2011/026987 A describes a prosthetic fabric (mesh) comprising an arrangement of yarns and barbs protruding outwards relative to a face of the fabric. The barbs, which serve as a fixation aid, may be formed from yarns or, as hooks produced from a biocompatible material, are attached to the fabric. The other face of the fabric comprises a microporous layer made of a bio-resorbable material. The barbs are generally sharp due to a cutting process. To decrease the tendency of this product to adhere to itself, e.g. when folded for delivery through a trocar sleeve, the barbs are covered with a coating made of a water-soluble material, which dissolves during the surgical operation. Nevertheless, the handling of the product may be difficult.

U.S. Pat. No. 7,331,199 discloses a prosthetic knit for medical or surgical use which comprises spiked naps made from loops of the knit structure. The spiked naps protrude perpendicularly from the sheet defined by the knit, have a substantially rectilinear body and a free end with a head, which is somewhat wider than the rectilinear body. The spiked naps provide grip properties and can be used to attach two parts of the knit structure to each other.

The problem of the invention is to provide a surgical implant, in particular for the repair of hernias, which reduces the need for suturing and can be handled during a surgical procedure in an easy, quick and safe way.

This problem is solved by a surgical implant according to claim 1. Advantageous embodiments of the invention follow from the dependent claims. Claim 19 is directed to a process of manufacturing such surgical implant.

The surgical implant according to the invention comprises a basic structure having a first face, wherein the basic structure preferably comprises a mesh-like structure having the first face and a second face opposite to the first face. A resorbable (bio-absorbable) film is attached to the first face of the basic structure. A plurality of solid protrusions emerges from the film in a direction away from the basic structure. The protrusions comprise a shape defined by a respective body and a respective head, wherein the body emerges from the film and terminates in the head, and the head projects laterally with respect to the body.

The protrusions are made of solid material, they are not hollow. In this way, their resistance to shear in a plane in parallel to the film is increased. The body of a protrusion may comprise a foot (adjacent to the film) and a stem-like part, but designs without a well-defined foot are conceivable as well. The head of a protrusion projects laterally (i.e. generally in a direction in parallel to the local area of the film where the protrusion emerges) with respect to the body, i.e. with respect to the end of the body where the head begins. This does not exclude a foot portion of the body having a greater lateral extension than the head. Moreover, it is not required that the head projects laterally with respect to the body along the total circumference of the head. In advantageous embodiments of the invention, at least part of the protrusions comprises a mushroom-like shape. In addition to the protrusions described so far, the surgical implant may comprise protrusions which are designed in a different manner.

The surgical implant according to the invention may have a generally areal shape and may be used as a hernia implant exhibiting the additional benefit of self-fixation. Upon slightly pressing the implant, the solid protrusions emerging from the film are able to mechanically grip into soft tissue (e.g., facial tissue, muscle tissue, fatty tissue) and, due to their shape, provide to the film enhanced resistance to shear forces as well as peel forces. Thus, the basic structure to which the film is attached is prevented from migration and is securely held in its position during the initial critical wound healing period (tissue integration period). Since the film is resorbable, any mechanical irritation due to the protrusions will disappear during the healing process. Generally, there is no need for sutures for securing the implant. This provides a better comfort to the patient and reduces the risk of chronic pain associated with conventional fixation by sutures.

During the surgical procedure, the surgical implant according to the invention can be handled in a convenient manner. Generally, because of the design of the protrusions, the implant does not tend to adhere to itself when in a rolled or folded state. Thus, the implant is well suitable for laparoscopic placement. It can be forwarded to the site of surgery through a trocar sleeve and easily be unrolled or unfolded thereafter, without sticking to itself. Moreover, although the implant is self-fixating, it allows for repositioning as it is generally possible to peel the implant off from bodily tissue and position it again at a different or displaced location. Since it is generally not required to fix the implant by sutures, the surgical procedure tends to be shorter. If nevertheless desired, the implant can be additionally fixated by, e.g., suturing.

If the surgical implant is designed as a soft-tissue implant, e.g. a hernia implant, and is adapted to fix itself at least partially in soft tissue such as muscle or fat, the friction between the surgical implant and the soft tissue can be increased in at least one direction (measured essentially in the plane of the implant) by a factor of 2 or more, compared to a corresponding implant without protrusions.

As already mentioned, in advantageous embodiments of the invention the basic structure comprises a mesh-like structure, which term is to be understood rather general and includes, e.g. meshes (surgical meshes), tapes, perforated films, non-woven fabric, woven fabric, knitted sheets, knitted tapes, braided sheets, braided tapes, collageneous fibrillar sheets, mesh pouches and mesh plugs. In mesh pouches or mesh plugs, a mesh is folded or rolled and optionally fixed to itself at some points or areas, or a corresponding structure is provided from several mesh pieces. It is also conceivable to use the surgical implant according to the invention as, e.g., a pelvic mesh or a breast implant. In such cases, the basic structure of the implant is adapted to the desired purpose. Generally, it is not required that a resorbable film is attached to the entire first (or second) face of the mesh-like structure or, more general, of the basic structure.

In advantageous embodiments of the invention, the protrusions consist of the same material as the film. The film and the protrusions can be made in one piece. A process of manufacturing such an implant is described further below.

As already mentioned, the head of a protrusion laterally projects with respect to its body. In advantageous embodiments, the smallest cross-sectional area of the body, measured in a plane perpendicular to a longitudinal axis of the body, is smaller than the greatest cross-sectional area of the head, measured in a plane perpendicular to a longitudinal axis of the head, and the height of the body, measured along the longitudinal axis of the body, can be greater than the thickness of the head, measured along the longitudinal axis of the head, by at least a factor of 2, preferably by at least a factor of 3. That means, the head of the protrusion is basically "flat".

Depending on the purpose of the surgical implant according to the invention, the dimensions as well as the areal density of the protrusions may vary over large ranges. Preferably, the height of a protrusion (body plus head) is in the range of from 20 μm to 5000 μm. All intermediate values between these limits are disclosed as well, e.g. ranges of from 100 μm to 500 μm or of from 200 μm to 400 μm or of from 20 μm to 250 μm. The protrusions may have a density, e.g., in the range of from 0.5 protrusions/mm$^2$ to 5 protrusions/mm$^2$ or of from 2 protrusions/mm$^2$ to 4 protrusions/mm$^2$. The allowable size or diameter of a head of a protrusion also depends on the areal density. A typical head diameter is, e.g., 200 μm. The protrusions can be arranged in a rather dense manner. Moreover, it is possible to chose a pattern for the arrangement of the protrusions in a given implant.

The protrusions, which have a respective longitudinal axis, can emerge from the film at an angle relative to the surface of the film in the range, e.g., of from 50° to 90° or from 70° to 90°, which includes perpendicularly (90°) rising protrusions.

The film of the surgical implant may comprise pores in between the protrusions, wherein preferably the pores have a size (typical dimension, e.g. diameter of a circular pore) in the range of from 0.5 mm to 50 mm or of from 2 mm to 20 mm. Such pores facilitate tissue ingrowth before the film is resorbed. Moreover, depending on the shape and pattern of the pores, the elasticity of the film can be improved, e.g. for adaption to a generally high elasticity of the basic structure used in the surgical implant.

At least one pore may comprise at least one projection emerging from an edge of the pore into an area of the pore and consisting of the material of the film. Such projections are described in DE 10 2012 005 978 A and can serve to improve the self-fixation effect of the implant.

The thickness of the film can be, e.g., in the range of from 10 μm to 250 μm or in the range of from 20 μm to 200 μm, but other values are conceivable as well. The thickness of the film may vary in the implant. Moreover, the thickness of the film in the finished implant may be different from the thickness of an initial film layer used when the implant is manufactured, for example when material of such film layer is used to form the protrusions, as in examples described further below.

If the basic structure comprises a mesh-like structure, the surgical implant according to the invention may comprise a second film, in addition to the resorbable film bearing the protrusions and attached to the first face of the basic structure. The second film is attached to the second face of the mesh-like structure and may be resorbable and/or may have anti-adhesive properties. If desired, the second film can also be provided with protrusions, which emerge from the second film in a direction away from the mesh-like structure, preferably in a similar manner as the protrusions emerging from the first film.

In another advantageous embodiment of the invention, the effect of two films provided with protrusions is achieved by one film. In this case, the basic structure is mesh-like and the film extends into the mesh pores present in the basic structure, wherein protrusions emerge from the film in both directions, away from the first face of the basic structure and away from the second face of the basic structure. An example of a manufacturing process for such implant is presented further below.

Suitable materials for the resorbable film are well known in the art. The selection of the film material depends, e.g., on the resorption period. Considering processes of manufacturing the implant according to the invention, it may also depend on the melting temperature of the film material relative to that of the material of the basic structure (see below). For example, the film may comprise poly-p-dioxanone ("PDS"), copolymers of glycolide and ε-caprolactone (e.g., "Monocryl" of Johnson & Johnson Medical GmbH) and/or copolymers of glycolide and lactide (in particular in the ratio 90:10, "Vicryl" of Johnson & Johnson Medical GmbH). Generally, a large variety of synthetic bioabsorbable polymer materials can be used, for example polyhydroxy acids (e.g., polylactides, polyglycolides, polyhydroxybutyrates, polyhydroxyvaleriates), copolymers of lactide and trimethylene carbonate, copolymers of glycolide, lactide and trimethylene carbonate, polycaprolactones, polydioxanones, synthetic (but also natural) oligo- and polyamino acids, polyphosphazenes, polyanhydrides, polyorthoesters, polyphosphates, polyphosphonates, polyalcohols, polysaccharides, polyethers. However, naturally occurring materials such as collagen and gelatine or naturally derived materials such as bioabsorbable gel films cross-linked with omega 3 fatty acids or oxygenized regenerated cellulose (ORC) are conceivable as well.

The basic structure of the surgical implant, e.g. a surgical mesh, can be resorbable, non-resorbable or partially resorbable. Generally, it is flexible and, as a mesh, has an areal basic shape. For example, it can be based on a commercially available hernia repair mesh made, e.g., by warp-knitting.

Suitable materials for the basic structure are well known in the art. Non-resorbable or very slowly resorbable substances include, e.g., polyalkenes (e.g. polypropylene or polyethylene), fluorinated polyolefins (e.g. polytetrafluoroethylene (PTFE) or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Other advantageous materials, many of them being resorbable, include polyhydroxy acids, polylactides, polyglycolides, polyhydroxybutyrates, polyhydroxyvaleriates, polycaprolactones, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, cellulose, bacterial cellulose, polyamides, aliphatic polyesters, aromatic polyesters, copolymers of polymerizable substances thereof, resorbable glasses. Particularly advantageous materials include polypropylene (non-resorbable), blends of polyvinylidene fluoride and copolymers of vinylidene fluoride and hexafluoropropene (non-resorbable, e.g. "Pronova" of Johnson & Johnson Medical GmbH) PTFE (non-resorbable; including ePTFE and cPTFE), polysilicones (non-resorbable), poly-p-dioxanone ("PDS", resorbable), copolymers of glycolide and lactide (resorbable), in particular copolymers of glycolide and lactide in the ratio 90:10 ("Vicryl", resorbable), copolymers of lactide and trimethylene carbonate (resorbable), copolymers of glycolide, lactide and trimethylene carbonate (resorbable), copolymers of glycolide and ε-caprolactone ("Monocryl", resorbable). Biologic materials such as allograft and xenograft are conceivable as well.

For the second film (see above), the same materials can be contemplated as for the (first) film, depending on the desired properties. It is also conceivable to use, for the second film, a different material, e.g. in order to achieve certain anti-adhesive properties.

A surgical implant according to the invention may be manufactured by using the following steps: providing a flexible mold containing an array of cavities, each cavity having the shape of one protrusion; filling the mold with a fluid material which forms the protrusions and the film; hardening the fluid material; attaching the film to a basic structure (e.g., a mesh), with the protrusions pointing away from the basic structure; removing the mold.

The order of how these steps are listed above does not necessarily represent the sequence in which the steps are executed when the process of manufacturing according to the invention is performed, which will become clearer from the examples explained below.

The mold preferably comprises silicone, polyurethane, natural rubber and/or synthetic rubber. Silicone, e.g., is very flexible and thermo-stable. The mold is basically planar and provides a surface for forming the film. Extending from this surface, there are cavities, each one having the shape of one protrusion. A silicone mold, e.g., can be manufactured, e.g., by using a mechanically produced master (a positive of the array of protrusions) of a metal or a polymer as a master mold, which is filled with silicone precursors and reacted. Due to the large elasticity of silicone, the master mold can be removed after the reaction is finished.

The steps of filling the mold with a fluid material which forms the protrusions and the film, of hardening the fluid material and of attaching the film to a mesh (serving as basic structure) may be performed essentially at the same time, for example in the following way: A film material (e.g. of poly-p-dioxanone) is placed on the mold, and a mesh (e.g. of polypropylene) having a higher melting point than the film material is placed on top of the film material. After closing the mold by placing a counter-piece (e.g., an elastic press pad having a lower Shore hardness than the Shore hardness of the mold) on the mesh, the assembly is heated under pressure so that the film material melts or at least gets very soft and presents a fluid material which fills the cavities and forms the desired film, whereas one face of the mesh (which keeps its shape) is embedded in the film. In this example, hardening is achieved by cooling the assembly well below the melting or softening point of the film. At the end, the mold is removed, which is possible because of the high elasticity of the silicone, in spite of the presence of the heads of the protrusions.

Depending on the materials used and the details of the process, the hardening step may be performed by evaporation of a solvent, by cooling (as in the example above) or by reacting reactants forming the film and the protrusions.

It is also possible to form the film including the protrusions in a first step (e.g., as described above but without using a mesh inside the mold) and, after removing the mold, to attach the film to a mesh (or another kind of basic structure) in a second step, e.g. by placing and melting another film (having a low melting point) between the film and the mesh (basic structure) as a kind of melt-glue.

If the surgical implant comprises a second film, both films including the protrusions can be made and attached to a mesh by using an assembly as that described above, wherein the counter-piece comprises a mold for the second film. Alternatively, the second film (or both films) can be made separately and attached to the mesh afterwards.

A surgical implant comprising a mesh-like basic structure with a film extending into the mesh pores and protrusions emerging from the film in both directions can be manufactured, e.g., in the following way: A layer of film material and a mesh-like basic structure are arranged facing each other and placed between two molds, each being provided with an array of cavities corresponding to the protrusions to be formed. When the temperature is raised and both molds are pressed towards each other, the film layer melts or gets very soft and film material sucks into the pores of the basic structure and into the cavities of both molds. If the original film layer contains enough material, the material will fill the cavities, whereas part of the material will remain in the mesh pores. When the assembly is cooled and the molds are removed, the resulting surgical implant comprises protrusions emerging from the film in both directions, i.e. away from the first face of the basic structure and away from the second face of the basic structure.

In the following, the invention is described in more detail by means of embodiments. The drawings show in FIG. 1 a schematic three-dimensional view of an embodiment of the surgical implant according to the invention, FIG. 2 an explosion view of another embodiment of the surgical implant according to the invention, the insert displaying a magnified view, FIG. 3 a three-dimensional view of the embodiment according to FIG. 2, FIG. 4 an explosion view of another embodiment of the surgical implant according to the invention, the insert displaying a magnified view, FIG. 5 several views of an embodiment of a protrusion, i.e. in part (a) a three-dimensional view from the top side, in part (b) a side view, in part (c) a three-dimensional view from the bottom side and in part (d) a longitudinal-sectional view, FIG. 6 several views of another embodiment of a protrusion, i.e. in part (a) a three-dimensional view from the top side, in part (b) a side view and in part (c) a three-dimensional view from the bottom side, FIG. 7 several views of another embodiment of a protrusion, i.e. in part (a) a three-dimensional view from the top side, in part (b) a side view, in part (c) a three-dimensional view from the bottom side and in part (d) a longitudinal-sectional view, FIG. 8 several views of another embodiment of a protrusion, i.e. in part (a) a three-dimensional view from the top side, in part (b) a side view and in part (c) a three-dimensional view from the bottom side, FIG. 9 several views of another embodiment of a protrusion, i.e. in part (a) a three-dimensional view from the top side, in part (b) a side view and in part (c) a three-dimensional view from the bottom side, FIG. 10 several views of another embodiment of a protrusion, i.e. in part (a) a three-dimensional view from the top side, in part (b) a side view and in part (c) a three-dimensional view from the bottom side, and FIG. 11 a schematic explosion view representation of an example of a process of manufacturing an implant according to the invention.

FIG. 1 illustrates an embodiment of a surgical implant, designated by reference numeral 1, and shows part of the implant in a schematic three-dimensional view.

The surgical implant 1 comprises a basic structure 2 designed as a surgical mesh having a first face 4 and a second face 5. In the embodiment, an "Ultrapro" mesh marketed by Johnson & Johnson Medical GmbH is used as the mesh 2, which comprises filaments of "Monocryl" (see above) and filaments of polypropylene.

To the first face 4 of the basic structure 2, there is attached a resorbable film 6 which includes pores 7 having a hexagonal shape and being arranged in a regular pattern. In the embodiment, the film 6 is made of dyed (violet) poly-p-dioxanone and has a thickness of 150 μm.

A plurality of solid protrusions 8 emerges from the film 6 in a direction away from the basic structure 2. In the embodiment, the protrusions comprise a mushroom-like shape, defined by a respective body and a respective head, in which the body emerges from the film and terminates in the head and wherein the head projects laterally with respect to the body.

Further below, several embodiments of protrusions will be explained in more detail, see FIGS. 5 to 10. And the manufacturing of a surgical implant similar to that shown in FIG. 1 will be illustrated by means of examples.

Figure 2:
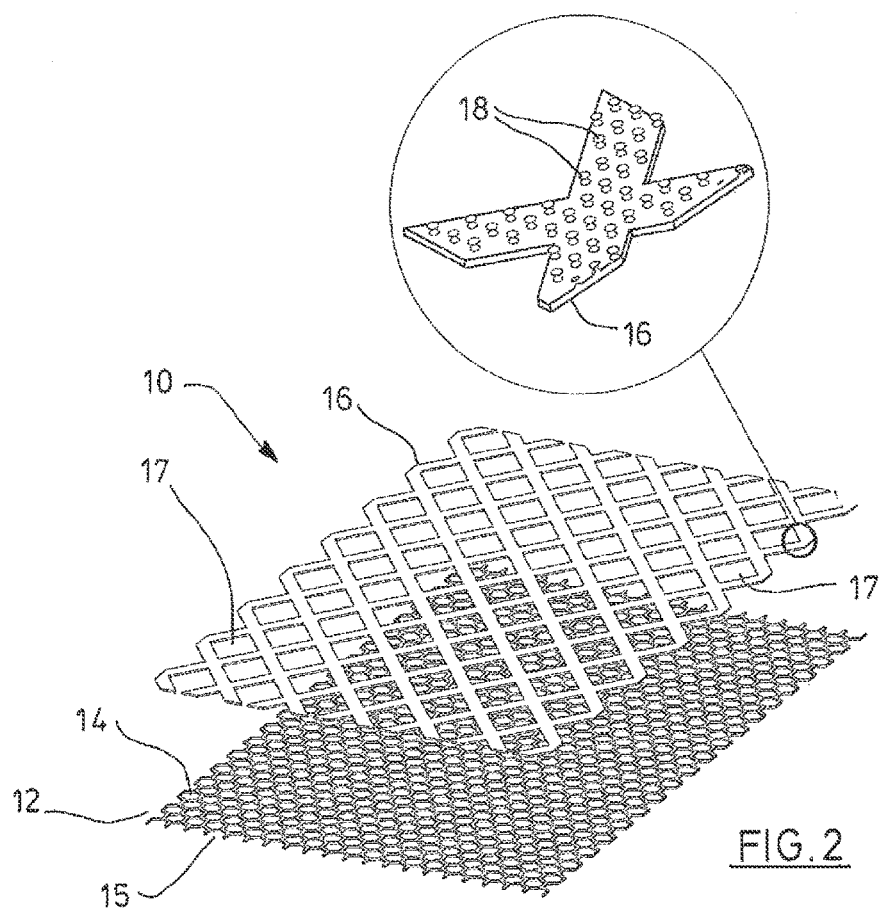

FIG. 2 shows another embodiment of a surgical implant, designated by reference numeral 10, in an exploded view. In this case, a basic structure 12 is designed as a surgical mesh having a first face 14 and a second face 15. A film 16 made of a resorbable material, e.g. poly-p-dioxanone, comprises relatively large pores 17 of rectangular shape.

In the areas between the pores 17, protrusions 18 emerge from the surface of the film 16, away from the basic structure 12. The insert is an enlarged view of a small part of the film 16 illustrating the protrusions 18.

Figure 3:
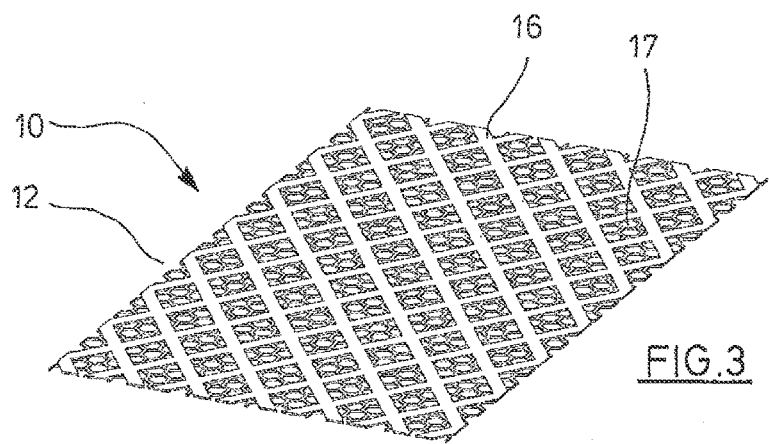

FIG. 3 shows the surgical implant 10 of FIG. 2 in the assembled state, in which the film 16 is attached to the first face 14 of the basic structure 12. The protrusions 18 are too small to be visible in this scale.

Figure 4:
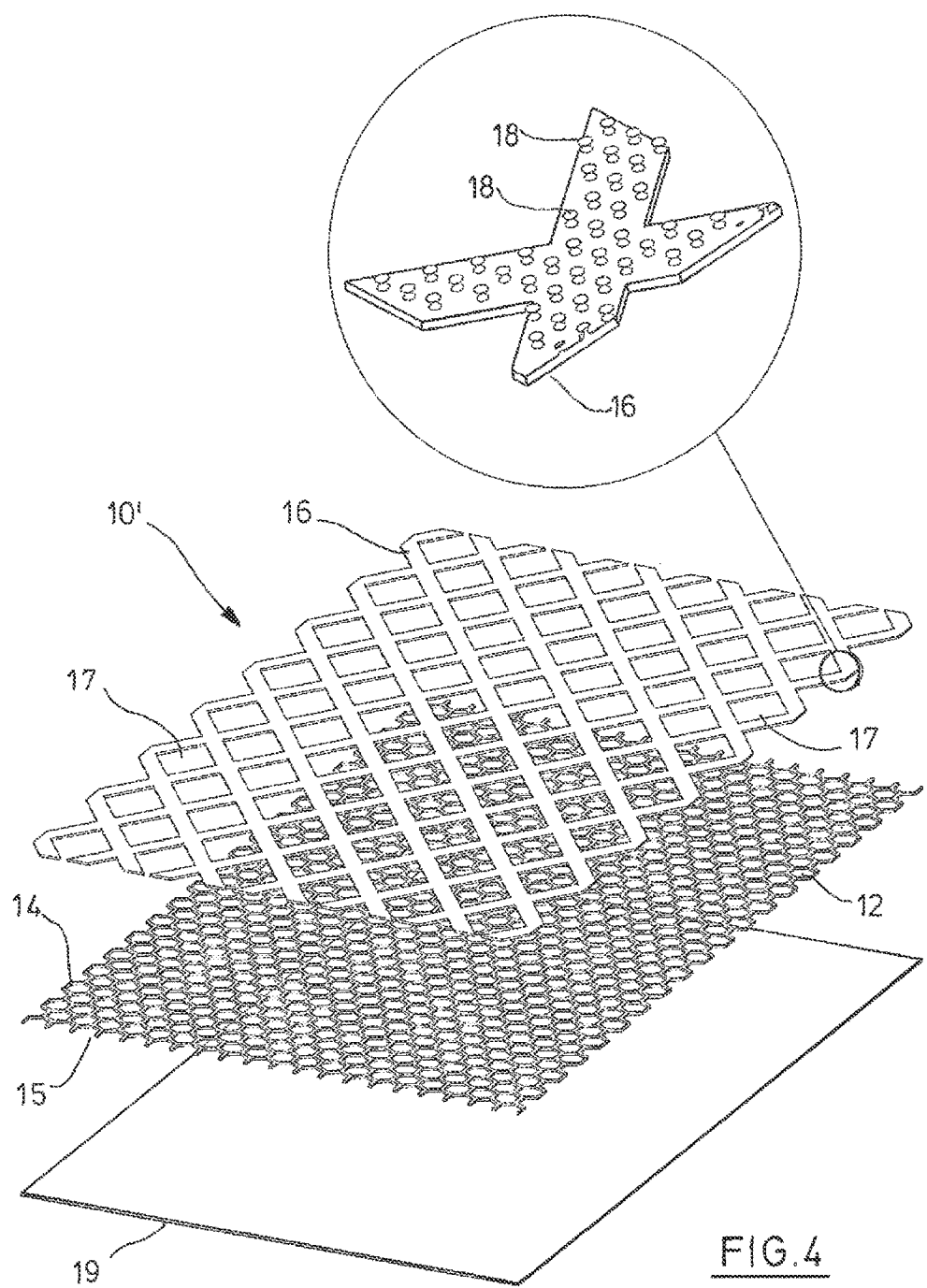

FIG. 4 illustrates another embodiment of a surgical implant, designated by reference numeral 10', which is very similar to surgical implant 10 of FIGS. 2 and 3. In contrast to surgical implant 10, however, surgical implant 10' comprises a second film 19 attached to the second face 15 of the basic structure 12. In the embodiment, the second film 19 is non-porous and has anti-adhesive properties in order to prevent bodily tissue from growing into the basic structure 12 via its second face 15.

When tested on pig belly, the protrusions 8, 18 resulted in a substantial increase of frictional forces on fascia and muscle. In contrast thereto, smooth films of poly-p-dioxanone as well as surgical meshes designed as pure textile meshes did not exhibit much frictional resistance to shear forces.

Figure 5:
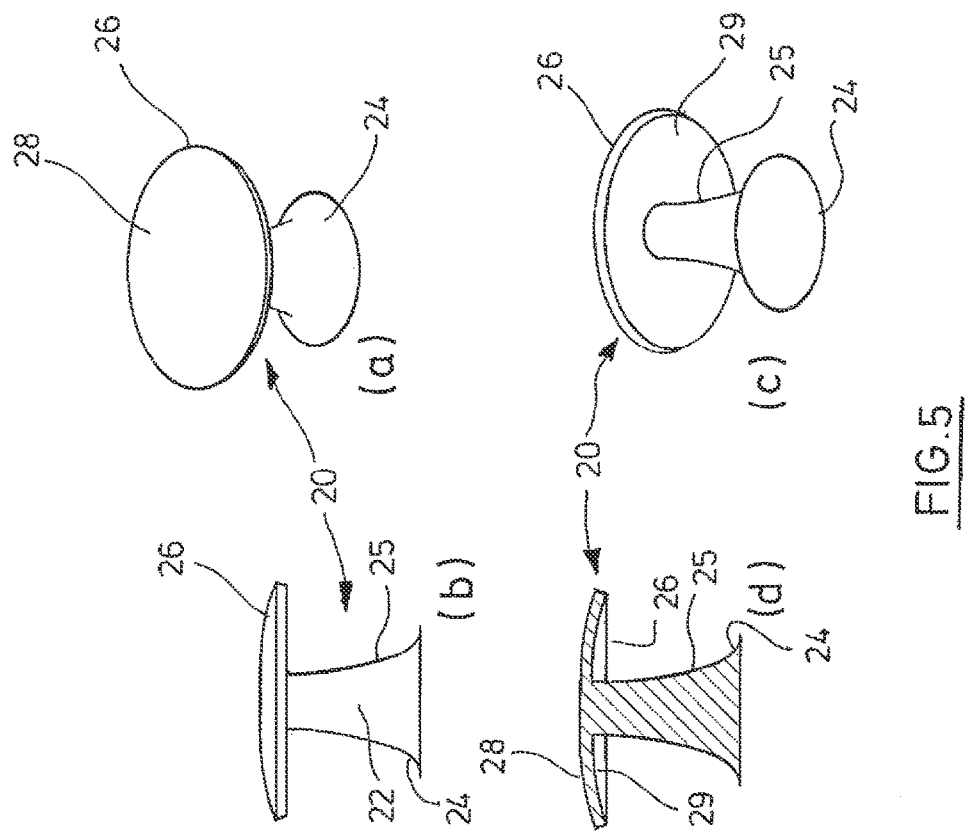

FIG. 5, in parts (a) to (d), displays a protrusion 20 in several enlarged views. The protrusion 20 comprises a body 22 including a foot 24 having an enlarged cross-sectional area and a stem 25. The body 22 terminates in a head 26 having a convex upper face 28 and a concave lower face 29, see in particular FIG. 5(d). The protrusion 20 has a mushroom-like shape in which the head 26 laterally projects with respect to the body 22 along the entire periphery of the head 26. In the embodiment, the protrusions 20 are made in one piece with the film from which the protrusions 20 emerge.

Figure 6:
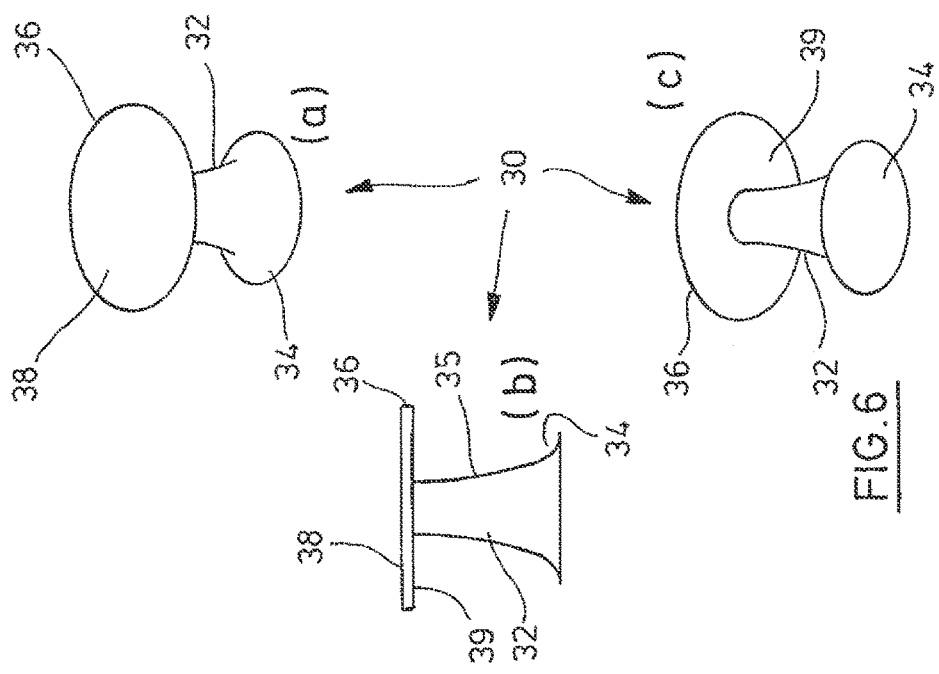

FIG. 6 illustrates, in parts (a) to (c), a protrusion 30 as another embodiment. The protrusion 30 comprises a body 32 including a foot 34 and a stem 35 as well as a head 36. In this case, the upper face 38 and the lower face 39 of head 36 are flat, as best visible in FIG. 6(b).

Figure 7:
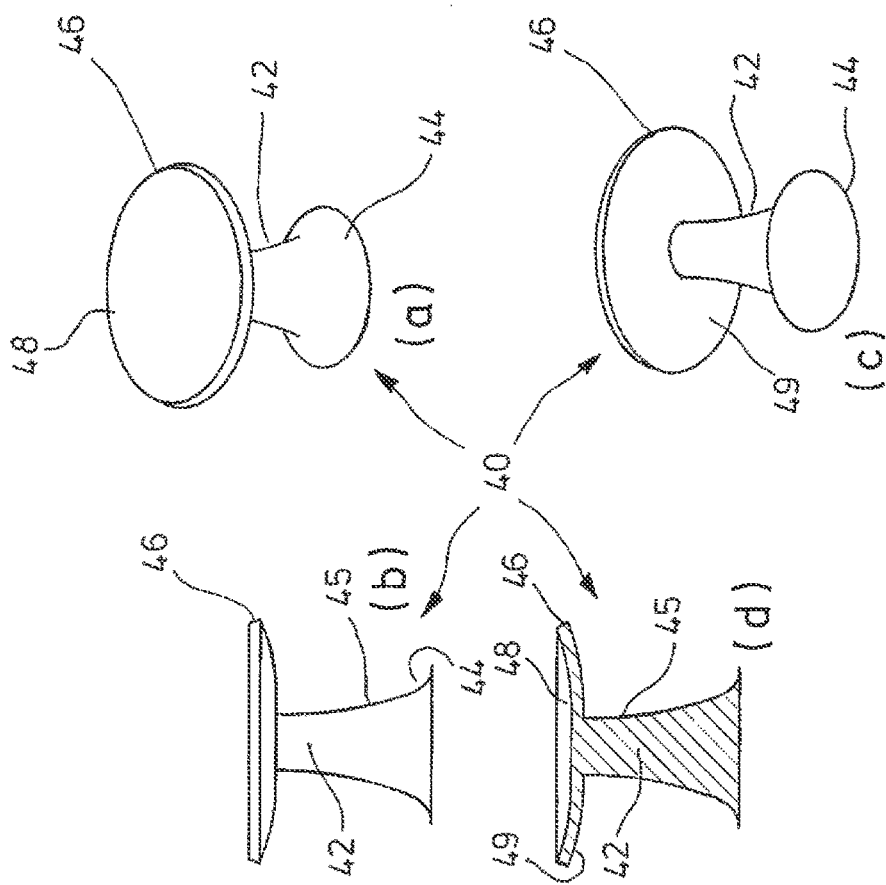

FIG. 7, in parts (a) to (d), shows a protrusion 40, which comprises a body 42 (including a foot 44 and a stem 45) as well as a head 46 having a concave upper face 48 and a convex lower face 49, as best visible in FIG. 7(d).

Figure 8:
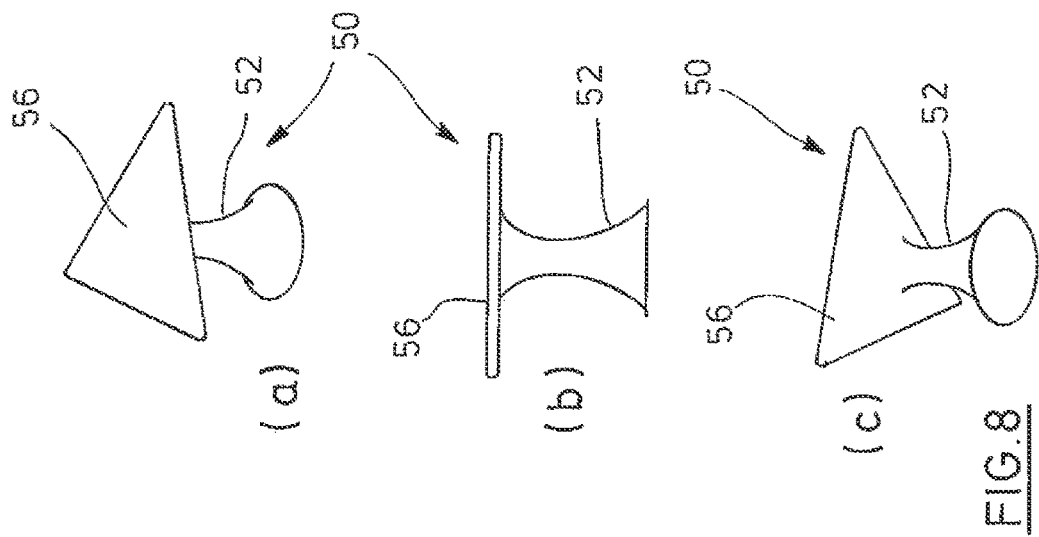

FIG. 8, in parts (a) to (c), displays a protrusion 50, which comprises a body 52 and a head 56 of a triangular basic shape.

In the embodiment shown in FIG. 9, in parts (a) to (c), a protrusion 60 comprises a body 62 with a stem 64. Along most of its length, the stem 64 has a cylindrical shape and then, in a transition region 65, curves outwardly until it reaches the edges of a head 66 of a square basic shape.

FIG. 10, in parts (a) to (c), shows a protrusion 70 having a cylindrical body 72 (without a foot) and a flat head 76 of hexagonal basic shape.

Many other embodiments of protrusions are conceivable as well. Generally, the heads of the protrusions grip into bodily tissue when the surgical implant in question is placed in a surgical procedure, which significantly increases frictional forces and stabilizes the position of the implant. To this end, it is not required that, in each protrusion, the head projects laterally with respect to the body along the entire periphery of the head. In the case of such asymmetric shapes, the heads of the protrusions may be aligned in the same direction or in different directions. Typical dimensions of the protrusions and ranges for the areal density of the protrusions have already been indicated further above. For example, protrusions may have a height from 100 μm to 500 μm and a density from about 0.5 protrusions/mm$^2$ to 5 protrusions/mm$^2$.

Figure 11:
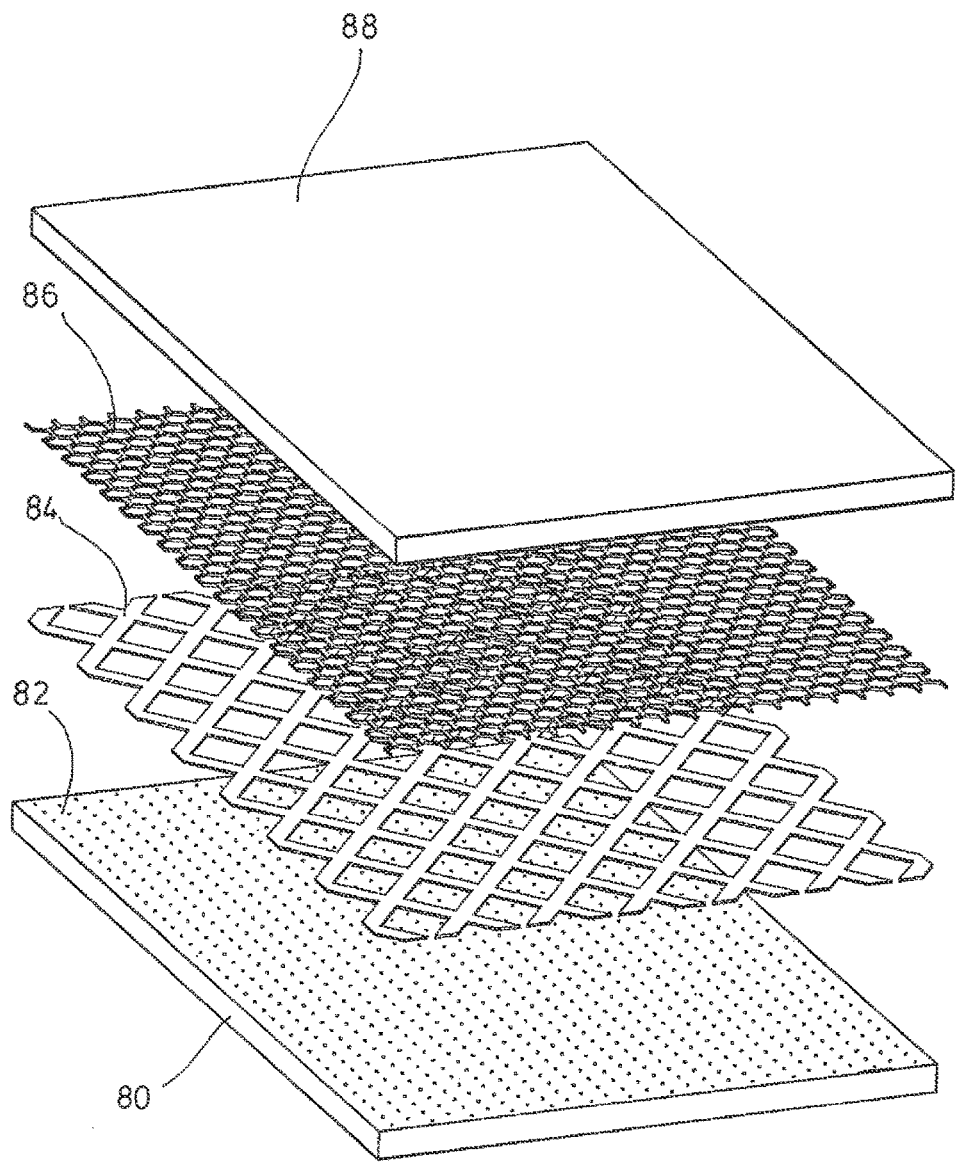

FIG. 11 illustrates, in a schematic way, an example of a process of manufacturing a surgical implant like the surgical implant 1 or the surgical implant 10.

At first, in a separate procedure, a flexible mold 80 is prepared, which contains an array of cavities 82, each cavity having the shape of one protrusion. Such a mold can be made, e.g., of silicone or polyurethane. The following example shows the preparation of a flexible silicone mold in a solvent-free process.

In the example, silicone (poly-dimethyls oxane, PDMS) and a starter are mixed in an appropriate ratio, as known in the art, degassed under vacuum and coated on a positive form. This positive form exhibits the array of the protrusions and can be made, e.g., by micro-milling of a polymer or metal block. A second vacuum-degassing step is recommended to remove trapped bubbles. The mixture is than cured by heat for a given time period. After curing, the positive form can be removed from the silicone mold 80. This can be accomplished without problems because of the flexibility of the silicone material of mold 80.

To manufacture the surgical implant, as shown in FIG. 11, first a resorbable film 84 is placed on top of the mold 80, facing the array of cavities 82. In the embodiment, the film 84 is made of poly-p-dioxanone (PDS), has a thickness of 150 μm and is provided with a regular pattern of rectangular or rhombic pores. Thereafter, a surgical mesh 86 like an "Ultrapro" mesh (see above) is placed on top of the film 84. To avoid shrinkage of the mesh 86 during the heat treatment described below, the mesh 86 might be thermo-set (heat shrinkage in advance) or might be kept in a holding frame.

A soft pad 88 is placed on top of the mesh 86. In the embodiment, pad 88 is an elastic press pad having a lower Shore hardness than the Shore hardness of mold 80. An additional soft pad (not shown in FIG. 11) might be positioned underneath mold 80.

Next, the array shown in FIG. 11 is pressed and heated for a predetermined period. In the example, in which a film 84 of PDS is used, the pressure can be in the range of from 1 bar to 50 bar (preferably 1 bar to 5 bar), the temperature in the range of from 105° C. to 140° C. (preferably about 120° C.) and the time period in the range of from 1 minute to 30 minutes (preferably about 5 minutes). Under these conditions, the PDS material of film 84 melts or gets very soft (i.e. it gets fluid by definition), whereas the mesh 86 essentially maintains its shape. The PDS material enters the cavities in the mold 80, thus forming the protrusions, and, at the same time, is safely attached to the mesh 86.

Thereafter, the assembly is cooled (under pressure) to room temperature or is placed between two cold metal plates for several minutes. After the PDS polymer has sufficiently solidified, the finished implant comprising the mesh 86 as basic structure and the film 84 with pores and with protrusions facing away from the mesh 86 can be easily removed from the flexible mold 80. Due to the flexibility of the silicone material of mold 80, this can be accomplished without damaging the laterally projecting heads of the protrusions.

The silicone mold 80 can be used several times.

If a surgical implant like implant 10' is to be manufactured, which comprises an additional film on the second face of the surgical mesh, such additional film can be placed between mesh 86 and pad 88 in the array according to FIG. 11. Again, the shaping of the protrusions and the attachment of the implant layers to each other can be achieved in essentially one step.

The process generally described by means of FIG. 11 allows for numerous variants. For example, a fluid material to be filled into the cavities of the mold and to form a non-porous film layer on top of the mold may be prepared by dissolving a polymer in a solvent. In this case, the step of hardening the fluid material involves evaporation of the solvent. Moreover, a film with protrusions may be attached to a basic structure via an intermediate layer serving as a melt glue. Or the steps of manufacturing the implant may be performed not quasi-simultaneously, but in a sequence, etc. Several aspects of the process in general have already been discussed further above.

Some more detailed examples follow.

EXAMPLE 1

Fabrication of a Silicone Mold Having Mushroom-Shaped Negatives

A micro-textured silicone mold was made from a 2-component silicone precursor kit (elastomeric kit). To this end, a positive form (master) of polypropylene comprising on one surface 288 mushroom-shaped protrusions/cm$^2$ (similar to those of FIGS. 5 to 7) with a total height of approximately 250 μm, a head diameter of approximately 375 μm, a stem diameter of approximately 200 μm and a foot diameter of approximately 340 μm was used. The liquid silicone elastomer was cast over the polypropylene master and, while keeping a horizontal position, cured at elevated temperatures (50° C. to 80° C.) in an oven for several hours. After cooling to room temperature, the silicone mold, comprising mushroom-shaped negatives of the protrusions, could be removed from the polypropylene master.

EXAMPLE 2

Fabrication of Poly-p-dioxanone Film/Polypropylene Mesh Laminates Having Mushroom-Shaped Protrusions on One Surface In a first step, rhombus-shaped pores (length 11.5 mm, width 9 mm) were cut in a regular pattern into a poly-p-dioxanone (PDS) film of thickness 150 μm using a laser cutter. The areas of the film between the pores had a width of about 2 mm.

This film was laminated onto a polypropylene mesh under controlled temperature (110° C.) and pressure (7.5 kN/cm$^2$) for 3.5 minutes using a heat press. To this end, the polypropylene mesh was positioned above a first elastic silicone press pad having a shore A hardness of 12±5. The PDS film was positioned above the polypropylene mesh and below a second elastic silicone press pad serving as a mold, having a shore A hardness of about 42±5 and comprising mushroom-shaped cavities for forming protrusions, allowing the filling up of the cavities during melting of the PDS film. The film/mesh laminate was cooled to 45° C. before decreasing pressure. Afterwards, the laminate was released by peeling the laminate away from the elastic silicone mold.

EXAMPLE 3

Fabrication of Poly-p-dioxanone Film/Polypropylene Mesh/Monocryl™ Film Laminates Having Mushroom-Shaped Protrusions on One Surface In a first step, rhombus-shaped pores (length 11.5 mm, width 9 mm) were cut in a regular pattern into a poly-p-dioxanone (PDS) film (film thickness 150 μm) using a laser cutter. The areas of the film between the pores had a width of about 2 mm.

This film was laminated on top of a polypropylene mesh having a "Monocryl" film (Polyglecaprone 25, copolymer of glycolide and ε-caprolactone, Johnson & Johnson Medical GmbH) of thickness 20 μm on its bottom side, wherein the polypropylene mesh and the "Monocryl" film were connected by melt-gluing of the PDS film during the lamination process. In detail: Lamination was performed under controlled temperature (110° C.) and pressure (7.5 kN/cm$^2$) for 3.5 minutes using a heat press. During lamination, the "Monocryl" film was positioned above a first elastic silicone press pad having a shore A hardness of 12±5. The polypropylene mesh was positioned above the "Monocryl" film. The PDS film was positioned above the polypropylene mesh and below a second elastic silicone press pad serving as a mold, having a shore A hardness of 42±5 and comprising mushroom-shaped cavities, allowing the filling up of the cavities during melting of the PDS. The film/mesh laminate was cooled to 45° C. before decreasing pressure. Afterwards, the laminate was released by peeling the laminate away from the elastic silicone mold.

EXAMPLE 4

Fabrication of Poly-p-dioxanone Film/Polypropylene Mesh Laminates Having Mushroom-Shaped Protrusions on Both Surfaces In a first step, rhombus-shaped pores (length 11.5 mm, width 9 mm) were cut in a regular pattern into a poly-p-dioxanone (PDS) film of thickness 150 μm using a laser cutter. The areas of the film between the pores had a width of about 2 mm.

This film was laminated onto a polypropylene mesh under controlled temperature (110° C.) and pressure (7.5 kN/cm$^2$) for 3.5 minutes using a heat press. To this end, the polypropylene mesh was positioned above a first elastic silicone press pad having a shore A hardness of 12±5. The PDS film was positioned above the polypropylene mesh and below a second elastic silicone press pad serving as a mold, having a shore A hardness of about 42±5 and comprising mushroom-shaped cavities for forming protrusions, allowing the filling up of the cavities during melting of the PDS film. The film/mesh laminate was cooled to 45° C. before decreasing pressure.

In a second process step, a second PDS film (of thickness 150 μm and with pores as above) was positioned below the polypropylene mesh, and the first elastic silicone press pad having a shore A hardness of 12±5, positioned below the Polypropylene mesh, was replaced by a second elastic silicone press pad serving as a mold, having a shore A hardness of 42±5 and comprising mushroom-shaped cavities for forming protrusions, allowing the filling up of the cavities during melting of the second PDS film. The film/mesh laminate was again cooled to 45° C. before decreasing pressure.

Afterwards, the laminate was released by peeling the laminate away from the elastic silicone molds on the upper side and on the lower side.

EXAMPLE 5

Test of the Implant of Example 2 on Rat Skin

The implants from Example 2 were tested in a rat skin friction model as per WO 2006/092236 A1. An Utrapro™ mesh without any film having protrusions served for comparison. The measured frictional force (in N) was plotted over the displacement path (in mm).

The implant from Example 2 showed a sharp increase in force to a maximum value of approximately 16N when the rat skin was moved over the surface having mushroom-shaped protrusions in a perpendicular manner. The increase is explained by the fact that, under the given test conditions, more and more protrusions locked into the rat skin tissue as displacement increased, until this applied to all the protrusions.

Under the same conditions, the maximum value of the force for the comparison mesh (Ultrapro™) was about 3N only.

EXAMPLE 6

Test of the Implant of Example 2 on Pork Belly

The implant from Example 2 was placed in different layers of pork belly (fat contact, fascia contact, muscle contact). Slight pressure without pulling already resulted in a locking of the mushroom-shaped protrusions. With a pulling direction perpendicular to the orientation of the protrusions the implant was fixed. There was good adherence in different tissues (muscle, fascia, fat).

The invention claimed is:

1. A surgical implant, comprising
   a basic structure having a first face;
   a resorbable film attached to the first face of the basic structure, said film comprising a first material; and,
   a plurality of solid mushroom-shaped protrusions emerging from the film in a direction away from the basic structure, wherein the protrusions comprise the first material, and
   wherein the mushroom-shaped protrusions comprise a shape defined by a respective body and a respective head, the body emerging from the film and terminating in the head, and the head projecting laterally with respect to the body, and the head having a smooth upper face with a configuration selected from the group consisting of flat, convex, and concave, and wherein the protrusions are part of the film and the film and the protrusions are made in one piece, the protrusions configured to adhere and lock to tissue without penetrating the tissue such that pressure upon the protrusions causes the protrusions to lock to tissue.

2. A surgical implant according to claim 1, characterized in that at least part of the protrusions comprises a mushroom-like shape.

3. A surgical implant according to claim 1, characterized in that the smallest cross-sectional area of the body, measured in a plane perpendicular to a longitudinal axis of the body, is smaller than the greatest cross-sectional area of the head, measured in a plane perpendicular to a longitudinal axis of the head, and in that the height of the body, measured along the longitudinal axis of the body, is greater than the thickness of the head, measured along the longitudinal axis of the head, by at least a factor of 2, preferably by at least a factor of 3.

4. A surgical implant according to claim 1, characterized in that the protrusions have a height in one of the following ranges: 20 μm to 5000 μm, 100 μm to 500 μm, 200 μm to 400 μm.

5. A surgical implant according to claim 1, characterized in that the protrusions have a density in one of the following ranges: 0.5 protrusions/mm$^2$ to 5 protrusions/mm$^2$, 2 protrusions/mm$^2$ to 4 protrusions/mm$^2$.

6. A surgical implant according to claim 1, characterized in that the protrusions have a respective longitudinal axis which emerges from the film at an angle relative to the surface of the film in one of the following ranges: from 50° to 90°, from 70° to 90°.

7. A surgical implant according to claim 1, characterized in that the film comprises pores in between the protrusions, wherein preferably the pores have a size in one of the following ranges: 0.5 mm to 50 mm, 2 mm to 20 mm.

8. A surgical implant according to claim 7, characterized in that at least one pore comprises at least one projection emerging from an edge of the pore into an area of the pore and consisting of the material of the film.

9. A surgical implant according to claim 1, characterized in that the basic structure comprises a mesh-like structure having the first face and a second face opposite to the first face.

10. A surgical implant according to claim 9, characterized by a second film, which is attached to the second face of the mesh-like structure, wherein optionally the second film has at least one of the following properties: being resorbable, being anti-adhesive.

11. A surgical implant according to claim 10, characterized in that a plurality of protrusions emerges from the second film in a direction away from the mesh-like structure.

12. A surgical implant according to claim 9, characterized in that the mesh-like basic structure comprises mesh pores and in that the film extends into the mesh pores, wherein protrusions as defined in claim 1 emerge from the film in both directions, away from the first face of the basic structure and away from the second face of the basic structure.

13. A surgical implant according to claim 1, characterized in that the film comprises a material selected from the following list: synthetic bioabsorbable polymer materials, polyhydroxy acids, polylactides, polyglycolides, copolymers of glycolide and lactide, copolymers of glycolide and lactide in the ratio 90:10, copolymers of lactide and trimethylene carbonate, copolymers of glycolide, lactide and trimethylene carbonate, polyhydroxybutyrates, polyhydroxyvaleriates, polycaprolactones, copolymers of glycolide and ε-caprolactone, polydioxanones, poly-p-dioxanone, synthetic and natural oligo- and polyamino acids, polyphosphazenes, polyanhydrides, polyorthoesters, polyphosphates, polyphosphonates, polyalcohols, polysaccharides, polyethers, collagen, gelatine, bioabsorbable gel films cross-linked with omega 3 fatty acids, oxygenized regenerated cellulose.

14. A surgical implant according to claim 1, characterized in that the basic structure comprises at least one of the materials selected from the following list: polyalkenes, polypropylene, polyethylene, fluorinated polyolefins, polytetrafluoroethylene, PTFE, ePTFE, cPTFE, polyvinylidene fluoride, blends of polyvinylidene fluoride and copolymers of vinylidene fluoride and hexafluoropropene, polyamides, polyurethanes, polyisoprenes, polystyrenes, polysilicones, polycarbonates, polyarylether ketones, polymethacrylic acid esters, polyacrylic acid esters, aromatic polyesters, polyimides, polyhydroxy acids, polylactides, polyglycolides, copolymers of glycolide and lactide, copolymers of glycolide and lactide in the ratio 90:10, copolymers of lactide and trimethylene carbonate, copolymers of glycolide, lactide and trimethylene carbonate, polyhydroxybutyrates, polyhydroxyvaleriates, polycaprolactones, copolymers of glycolide and ε-caprolactone, polydioxanones, poly-p-dioxanone, synthetic and natural oligo-and polyamino acids, polyphosphazenes, polyanhydrides, polyorthoesters, polyphosphates, polyphosphonates, polyalcohols, polysaccharides, polyethers, polyamides, aliphatic polyesters, aromatic polyesters, copolymers of polymerizable substances thereof, resorbable glasses, cellulose, bacterial cellulose, allograft, xenograft.

15. A surgical implant according to claim 1, characterized in that the surgical implant is adapted to be rolled or folded for laparoscopic placement, moved to a site of surgery through a trocar sleeve and unrolled or unfolded without sticking to itself.

16. A surgical implant according to claim 1, characterized in that the surgical implant is designed as a soft-tissue implant, preferably a hernia implant, and is adapted to fix itself at least partially in soft tissue such as muscle or fat, with the friction between the surgical implant and the soft tissue being increased in at least one direction by a factor of 2 or more, compared to a corresponding implant without protrusions.

17. A process of manufacturing a surgical implant according to claim 1, characterized by the steps:
providing a flexible mold containing an array of cavities, each cavity having the shape of one protrusion,
filling the mold with a fluid material which forms the protrusions and the film,
hardening the fluid material,
attaching the film to a basic structure, with the protrusions pointing away from the basic structure,
removing the mold.

18. A process according to claim 17, characterized in that the flexible mold comprises at least one of the following materials: silicone, polyurethane, natural rubber, synthetic rubber.

* * * * *